US010595776B1

(12) United States Patent
Selvaraj et al.

(10) Patent No.: US 10,595,776 B1
(45) Date of Patent: Mar. 24, 2020

(54) DETERMINING ENERGY EXPENDITURE USING A WEARABLE DEVICE

(71) Applicant: Vital Connect, Inc., Campbell, CA (US)

(72) Inventors: Nandakumar Selvaraj, San Jose, CA (US); Toai Doan, Saratoga, CA (US)

(73) Assignee: Vital Connect, Inc., San Jose, CA (US)

( * ) Notice: Subject to any disclaimer, the term of this patent is extended or adjusted under 35 U.S.C. 154(b) by 62 days.

(21) Appl. No.: 14/481,788

(22) Filed: Sep. 9, 2014

(51) Int. Cl.
*A61B 5/00* (2006.01)
*A61B 5/11* (2006.01)
*A61B 5/0205* (2006.01)
*A61B 5/0402* (2006.01)
*A61B 5/024* (2006.01)
*A61B 5/053* (2006.01)

(52) U.S. Cl.
CPC .......... *A61B 5/4866* (2013.01); *A61B 5/0022* (2013.01); *A61B 5/0205* (2013.01); *A61B 5/0402* (2013.01); *A61B 5/1118* (2013.01); *A61B 5/6801* (2013.01); *A61B 5/7225* (2013.01); *A61B 5/02405* (2013.01); *A61B 5/053* (2013.01)

(58) Field of Classification Search
CPC ... A61B 5/4866; A61B 5/0022; A61B 5/0205; A61B 5/0402; A61B 5/1118; A61B 5/6801; A61B 5/7225; A61B 5/02405; A61B 5/053
See application file for complete search history.

(56) References Cited

U.S. PATENT DOCUMENTS

| 6,506,152 | B1* | 1/2003 | Lackey | A61B 5/1118 128/921 |
| 2002/0133378 | A1* | 9/2002 | Mault | A61B 5/0002 705/3 |
| 2004/0133081 | A1* | 7/2004 | Teller | A61B 5/01 600/300 |
| 2004/0186390 | A1* | 9/2004 | Ross | A61B 5/083 600/532 |
| 2009/0062670 | A1* | 3/2009 | Sterling | A61B 5/04085 600/509 |
| 2010/0049004 | A1* | 2/2010 | Edman | A61B 5/1118 600/300 |
| 2011/0054359 | A1* | 3/2011 | Sazonov | A43B 3/0005 600/595 |
| 2011/0246123 | A1* | 10/2011 | DelloStritto | A61B 5/11 702/141 |

(Continued)

*Primary Examiner* — Gary Jackson
*Assistant Examiner* — Zahed Kabir
(74) *Attorney, Agent, or Firm* — Brundidge & Stanger, P.C.

(57) ABSTRACT

A method and system for determining energy expenditure (EE) are disclosed. The method comprises determining a plurality of sensor streams using a plurality of detected physiological signals and processing the plurality of sensor streams to determine the EE. The system includes at least one sensor to detect a plurality of physiological signals, a processor coupled to the at least one sensor, and a memory device coupled to the processor, wherein the memory device includes an application that, when executed by the processor, causes the processor to determine a plurality of sensor streams using a plurality of detected physiological signals and to process the plurality of sensor streams to determine the EE.

14 Claims, 11 Drawing Sheets

(56) References Cited

U.S. PATENT DOCUMENTS

| | | | |
|---|---|---|---|
| 2011/0276304 A1* | 11/2011 | Yin | A61B 5/1118 702/141 |
| 2012/0046113 A1* | 2/2012 | Ballas | A63F 13/00 463/43 |
| 2012/0084053 A1* | 4/2012 | Yuen | A61B 5/0002 702/160 |
| 2012/0149996 A1* | 6/2012 | Stivoric | A61B 5/01 600/301 |
| 2012/0215116 A1* | 8/2012 | Martikka | A61B 5/0205 600/484 |
| 2014/0073486 A1* | 3/2014 | Ahmed | A61B 5/02405 482/9 |
| 2014/0180033 A1* | 6/2014 | Altini | A61B 5/1118 600/301 |
| 2014/0275854 A1* | 9/2014 | Venkatraman | A61B 5/721 600/301 |
| 2014/0307927 A1* | 10/2014 | Folmer | A61B 5/7267 382/107 |
| 2015/0125832 A1* | 5/2015 | Tran | G09B 19/0092 434/127 |
| 2015/0164410 A1* | 6/2015 | Selvaraj | A61B 5/1121 600/509 |
| 2015/0164411 A1* | 6/2015 | Selvaraj | A61B 5/1121 600/301 |
| 2015/0272457 A1* | 10/2015 | Etemad | A61B 5/02438 600/509 |
| 2016/0058332 A1* | 3/2016 | Tan | A61B 5/0205 702/19 |
| 2016/0058371 A1* | 3/2016 | Singh Alvarado | A61B 5/0205 600/483 |
| 2016/0058372 A1* | 3/2016 | Raghuram | A61B 5/0205 600/595 |
| 2016/0287177 A1* | 10/2016 | Huppert | A61B 5/6833 |

* cited by examiner

DETERMINING ENERGY EXPENDITURE USING A WEARABLE DEVICE

FIELD OF THE INVENTION

The present invention relates to wearable sensor devices, and more particularly, to determining energy expenditure using a wearable device.

BACKGROUND

Obesity is a growing health care crisis in the US and around the world as more than two-thirds of US adults are overweight which has resulted in $147 billion dollars in 2008 in medical costs associated with obesity. The primary cause stems from poor dietary habits, lack of physical activity, and a lack of tools that accurately track and measure calorie intake and energy expenditures.

Conventional methods of measuring energy expenditures include direct calorimetry and indirect calorimetry but these conventional methods are very expensive, bulky, and uncomfortable for the users. Additionally, the conventional methods are impractical for continuous monitoring in free-living conditions as they require daily calibrations and professional interpretation and analysis of the data.

Conventional methods of estimating energy expenditures include estimations based on speed, physical activity, and heart rate. However, these conventional methods all require individual calibration and/or knowledge of individual/user parameters such as gender, age, weight, height, etc. Additionally, estimations using speed are inaccurate due to device variances, estimations using physical activity are inaccurate due to the inability to distinguish static exercise, and estimations using heart rate are challenging because it is difficult to continuously and accurately monitor the heart rate in free living conditions, and it further requires a cumbersome calibration procedure in order to customize to the individuals. Therefore, there is a strong need for a solution that overcomes the aforementioned issues. The present invention addresses such a need.

SUMMARY OF THE INVENTION

A method and system for determining energy expenditure (EE) are disclosed. In a first aspect, the method comprises determining a plurality of sensor streams using a plurality of detected physiological signals and processing the plurality of sensor streams to determine the EE.

In a second aspect, the system includes at least one sensor to detect a plurality of physiological signals, a processor coupled to the at least one sensor, and a memory device coupled to the processor, wherein the memory device includes an application that, when executed by the processor, causes the processor to determine a plurality of sensor streams using a plurality of detected physiological signals and to process the plurality of sensor streams to determine the EE.

BRIEF DESCRIPTION OF THE DRAWINGS

The accompanying figures illustrate several embodiments of the invention and, together with the description, serve to explain the principles of the invention. One of ordinary skill in the art readily recognizes that the embodiments illustrated in the figures are merely exemplary, and are not intended to limit the scope of the present invention.

DETAILED DESCRIPTION

Figure 1:
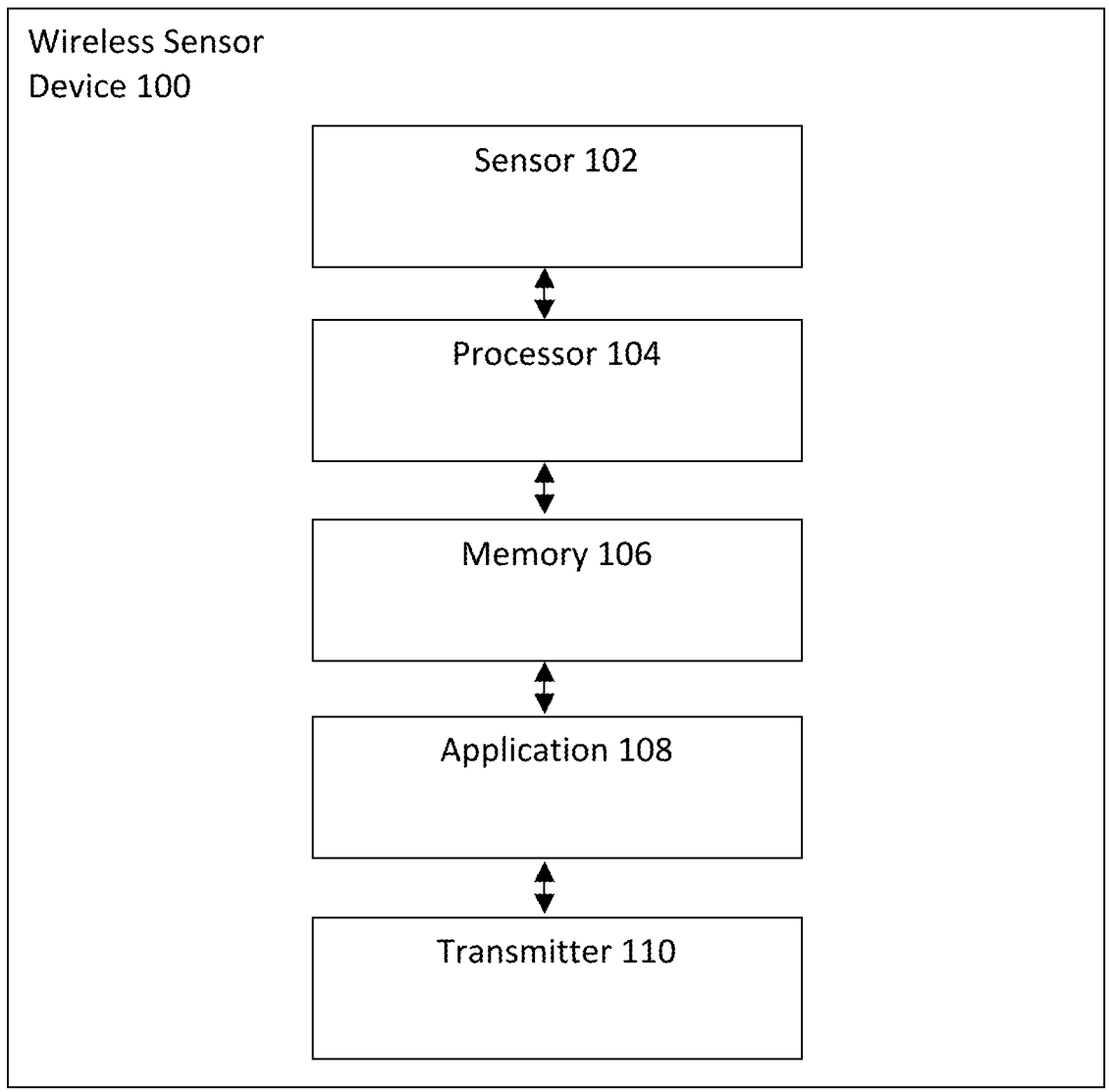
FIG. 1 illustrates a wireless sensor device for determining energy expenditure (EE) in accordance with an embodiment.

The present invention relates to wearable sensor devices, and more particularly, to determining energy expenditure using a wearable device. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Obesity is a growing health crisis in the US and around the world. According to the US Department of Health and Human Services, among adults aged 20 years or older, more than 1 in 3 adults are found to be obese (BMI over 30) and more than 2 in 3 adults in the US are found to be overweight (BMI over 25). Being overweight/obese is one of the leading risk factors for major health problems including hypertension, type-2 diabetes, coronary heart disease, stroke, sleep apnea, osteoarthritis, and certain types of cancer. Poor dietary choices, sedentary lifestyles, and a lack of physical activity/exercise primarily disrupt the energy balance which is the ratio of energy expended (or burned) to the energy intake (food consumed).

The energy expenditure (EE) rate of an individual can be measured using various techniques such as direct and indirect calorimetry and by using accelerometer sensors that measure human movements during activities. However, the techniques are expensive, cumbersome, and not practical for everyday continuous monitoring and the sensors rely on human body acceleration signals alone and thus do not provide accurate EE rates during active lifestyles. Specifically, human body acceleration signals that are obtained from sensors located on extremities/pockets of clothing do not provide accurate EE rates and cannot distinguish from isometric/static exercises.

The traditional EE prediction algorithms based on HR generally require a calibration procedure that is involved with data collection for sufficient time periods of resting and performing at least moderate level of intense exercises for each individual. The data collected is used to determine an empirical flex point of HR termed as "HRflex", which is calculated as the average value of the highest HR during rest period and the lowest HR value during exercises. When the HR is below the HRflex value, the EE is quantified as a constant derived using height, weight, age and gender of the subject and is independent of HR changes. When the HR is above the HRflex value, the EE is quantified as a linear function of HR.

The major limitations of the previously reported HRflex approach are as follows: the calibration of HRflex requires a test that should be sufficiently long enough to obtain reliable HRflex point for each individual; the reliability of HRflex point using a single calibration test is very limited, since the test needs to be repeated many instances of a day to account for the 24 hour HR variability; the test needs to be performed periodically to take the changes in endurance levels of an individual over time into account; the HRflex is time varying that depends on various factors including, basal heart rate, time of the day, activities involved and demographics; requirement of lengthy and periodic calibration tests weaken the usability; resting EE rate estimation as a constant (independent of HR) below HRflex point might also cause significant error in total daily expended energy estimates during the continuous assessment of cumulative EE.

A method and system in accordance with the present invention provides a wireless, portable, and wearable sensor device ("wearable device") that is in a patch form factor and that is attached to a user (patient) to automatically and continuously measure and quantify the energy expenditure (EE) rate of the user thereby enabling the user to continuously track the calories that they intake and expend during free-living conditions. The wearable device provides awareness about the user's energy restrictions, various patterns, and leads to healthier living.

The wearable device accurately measures and continuously monitors a user's heart rate (HR) over predetermined time periods (e.g. 24 hour periods) in free-living conditions in addition to detecting and measuring other physiological signals including but not limited to human acceleration signals, electrocardiogram, HR, and heart rate variability (HRV). Utilizing the measured physiological variables including but not limited to HR values and the body acceleration signals detected from the torso of the user, the wearable device then utilizes an algorithmic process for the accurate prediction of energy expenditure (EE) that is more accurate than devices that utilize purely activity based algorithmic processes that derive the body acceleration signals from extremities/pockets of clothing. The present algorithmic processes do not necessitate any separate calibration procedures, and overcome the limitations of the HRflex approach.

In one embodiment, the algorithmic process utilizes a piecewise linear regression model that includes at least one break point as a fraction of a normalized HR ($HR_{nu}$). The normalized HR ($HR_{nu}$) can be determined by various approaches including but not limited to the ratio of instantaneous HR to the maximal allowable heart rate of the individual ($HR_{max}$), or a fraction of heart rate reserve (HRR). The thresholds of the normalized HR ($HR_{nu}$) or the break points are learned from clinical trials with diverse demographic population and thus calibration procedures for determining break point(s) are not required.

In another embodiment, the nonlinear regression model comprises a plurality of models that combine continuous acceleration signals of the upper torso and HR values obtained by the wearable device and subject related demographic information like body mass index and age to accurately predict the energy expenditure (EE) of the user. The prediction model of this algorithmic process does not involve any break points and does not require any separate calibration procedures.

FIG. 1 illustrates a wireless sensor device 100 for energy expenditure (EE) prediction in accordance with an embodiment. The wireless sensor device 100 ("wearable device") includes a sensor 102, a processor 104 coupled to the sensor 102, a memory 106 coupled to the processor 104, an application 108 coupled to the memory 106, and a transmitter 110 coupled to the application 108. One of ordinary skill in the art readily recognizes that the wireless sensor device 10 can include other components and that the components of the wireless sensor device 100 can be coupled in a variety of different ways and that would be within the spirit and scope of the present invention.

In one embodiment, the wireless sensor device 100 is attached to a user to detect various physiological signals via the sensor 102. The sensor 102 obtains data from the user, which is transmitted to the memory 106 and in turn to the application 108 via the processor 104. The processor 104 executes the application 108 to process and analyze the data to obtain information regarding the user's health such as energy expenditure (EE). The information is transmitted to the transmitter 110 and in turn relayed to another user or device for further processing, analysis, and storage. In another embodiment, the transmitter 110 transmits the various detected physiological signals in raw form to a remote device/server (e.g., smartphone, cloud-based server, etc.) for further processing, analysis, and storage.

In one embodiment, the sensor 102 is any of a microelectromechanical system (MEMS) tri-axial accelerometer and an embedded sensor with electrodes and the processor 104 is a microprocessor. One of ordinary skill in the art readily recognizes that a variety of devices can be utilized for the sensor 102, the processor 104, the memory 106, the application 108, and the transmitter 110 and that would be within the spirit and scope of the present invention.

Additionally, one of ordinary skill in the art readily recognizes that a variety of wireless sensor devices can be utilized including but not limited to wearable devices, a wireless sensor device in a patch form-factor, the Vital Connect HealthPatch™ wearable device, electrocardiograph devices, tri-axial accelerometers, uni-axial accelerometers, bi-axial accelerometers, gyroscopes, and pressure sensors and that would be within the spirit and scope of the present invention.

In one embodiment, the HealthPatch™ wearable device is a disposable adhesive patch biosensor worn on the chest that incorporates two surface electrodes with hydrogel on the bottom, a battery, an electronic module with an embedded processor and other electronic components and circuitry, a MEMS tri-axial accelerometer, and a Bluetooth Low Energy (BLE) transceiver.

In one embodiment, the wearable device facilitates continuous and automated monitoring of a plurality of physiological signals including but not limited to heart rate (HR) values and acceleration signals. In this embodiment, after the wearable device detects the plurality of physiological signals via a plurality of internal and embedded sensors, the electronic module of the wearable device utilizes a plurality of firmware algorithms to process raw waveforms of the plurality of physiological signals and to transmit a stream of the processed physiological variables via the BLE transceiver/link as encrypted data to a relay such as a smartphone, where the live (real-time) streams of data can be viewed and stored.

To describe the features of the present invention in more detail, refer now to the following description in conjunction with the accompanying Figures.

The wearable device utilizes a plurality of sensors and at least one of a plurality of algorithmic processes to accurately predict the energy expenditure (EE) of a user. In one embodiment, the wearable device detects a user's HR values and acceleration signals using the plurality of sensors and combines and processes the HR values, the acceleration signals and user specific information utilizing the at least one of the plurality of algorithmic processes to determine the energy expenditure (EE) of the user. In one embodiment, the plurality of algorithmic processes includes a first algorithmic process, a second algorithmic process, and a third algorithmic process.

In one embodiment, the first and the second algorithmic processes utilize at least one break/flex point that splits the HR spectrum into two or more linear regression models. Selecting the break point (or flex point) as a function of HR requires frequent/periodic calibration. Therefore, in this embodiment, the break point is selected as a function of normalized heart rate ($HR_{nu}$). In one embodiment, the normalization of the heart rate is obtained as a function of basal heart rate. By using $HR_{nu}$ values, the calibration requirements for determining the break point are eliminated.

Figure 2:
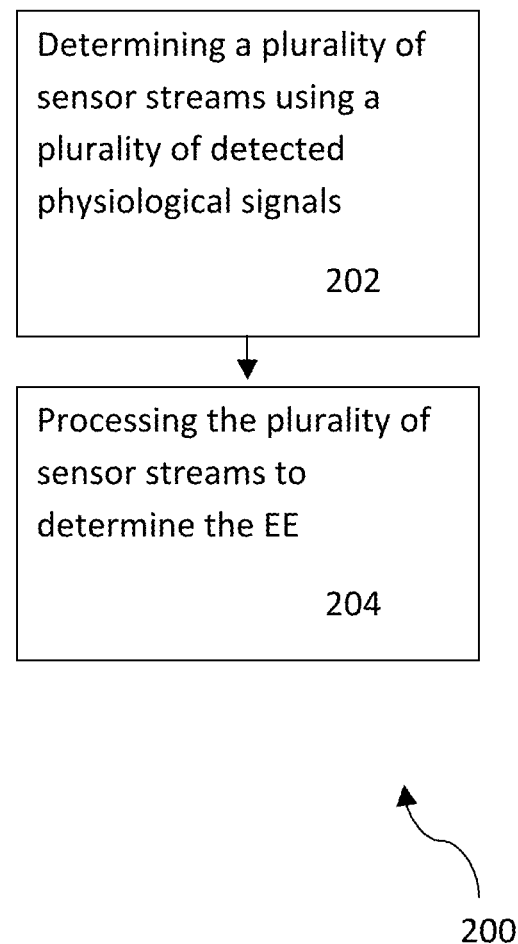
FIG. 2 illustrates a method for determining energy expenditure (EE) in accordance with an embodiment.

FIG. 2 illustrates a method 200 for determining energy expenditure (EE) in accordance with an embodiment. The method 200 includes determining a plurality of sensor streams using a plurality of detected physiological signals, via step 202, and processing the plurality of sensor streams to determine the EE rate, via step 204. The plurality of detected physiological signals are detected by a wearable device and include any of an electrocardiogram (ECG) signal and an acceleration signal and the plurality of sensor streams include any of body impedance, heart rate (HR), basal heart rate ($HR_b$), heart rate variability (HRV), and signal magnitude area (SMA). The processing step of the method 200 is performed by any of a wearable device, an external device, a relay/cloud processor, a smartphone device, and a cloud computing system.

In one embodiment, the processing step of the method 200 further comprises preprocessing the plurality of sensor streams, extracting features from the plurality of preprocessed sensor streams to provide a feature vector, and performing machine learning using the feature vector and a regression model to determine the EE rate. In one embodiment, the feature vector includes user/patient information related features including but not limited to any of height, weight, gender, age; heart rate related features including but not limited to any of heart rate (HR), normalized heart rate, and heart rate variability (HRV); and activity features including but not limited to signal magnitude area (SMA).

In one embodiment, the preprocessing step further comprises any of eliminating wearable device off instances using body impedance values, low-pass filtering the plurality of sensor streams, and normalizing the plurality of sensor streams, wherein the normalized HR heart rate ($HR_{nu}$) is determined as any of a function of basal heart rate ($HR_b$), a function of maximal allowable heart rate of the individual ($HR_{max}$), and as a fraction of heart rate reserve (HRR).

In a first embodiment, the regression model is a piecewise linear regression model with a break point, wherein the break point is a function of the normalized heart rate ($HR_{nu}$), wherein the break point splits the determination of the EE rate into two separate linear regression problems that correspond to the resting and active states.

In a second embodiment, the regression model is a piecewise linear regression model with two break points, wherein the two break points are a function of the normalized heart rate ($HR_{nu}$), wherein the two break points split the determination of the EE rate using three separate linear prediction models that correspond to resting, low-to-moderate intensity activities, and high intensity activities.

In a third embodiment, the relationship between EE rate and the physiological signals like HR is assumed to be nonlinear. The basis function of the regression model includes but is not limited to a quadratic polynomial, higher order polynomial, radial basis function, exponential, and sigmoidal function. This algorithmic approach does not involve any break point(s) and does not require any separate calibration procedures.

In one embodiment, a wearable device for determining energy expenditure (EE) comprises at least one sensor to detect a plurality of physiological signals, a processor coupled to the at least one sensor, and a memory device coupled to the processor, wherein the memory device includes an application that, when executed by the processor, causes the processor to perform the aforementioned steps of the method 200.

Figure 3:
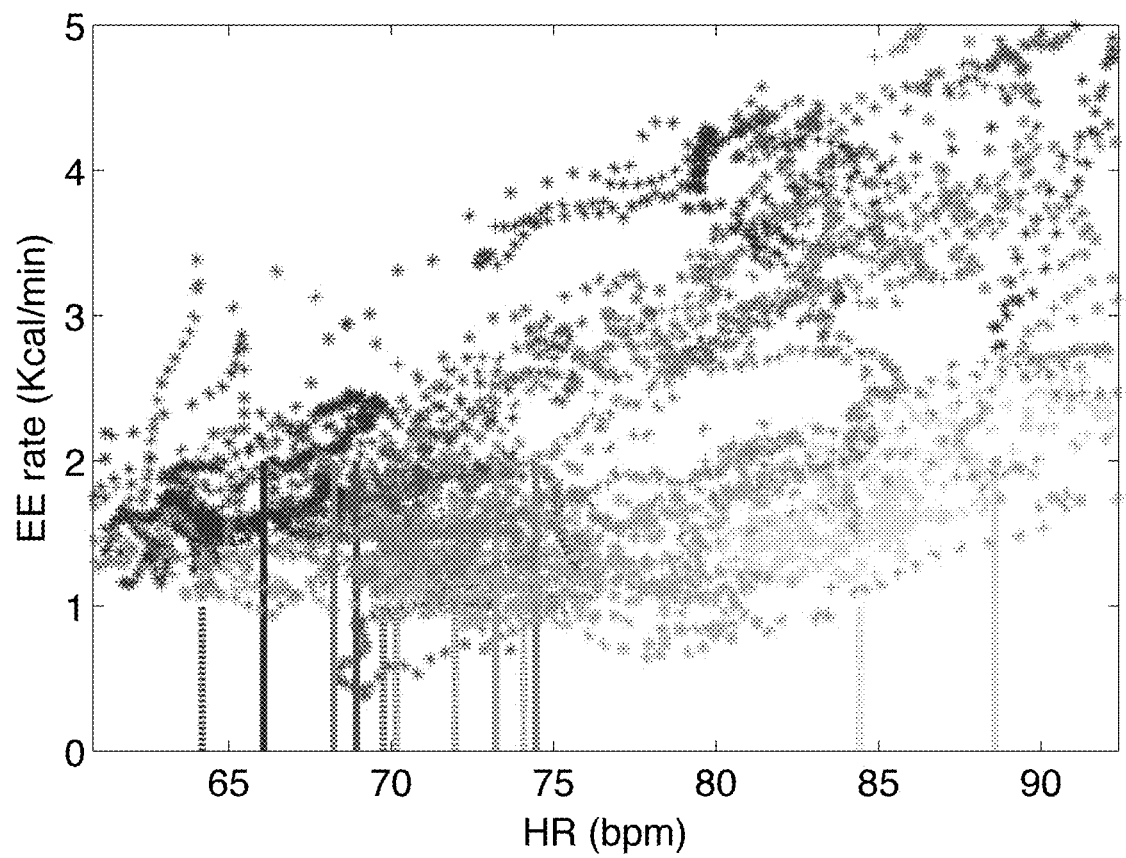
FIG. 3 illustrates a diagram of the relationship between energy expenditure (EE) rate and heart rate.

FIG. 3 illustrates a diagram 300 of the relationship between energy expenditure (EE) rate (in Kcal/min) and heart rate (in bpm). The heart rate (HR) values are obtained from a plurality of sample subjects that performed a calibration procedure involved with resting and exercises. The dotted vertical lines with y-scale magnitude "1" are referred to the basal HR estimates obtained in the plurality of sample subjects during resting period, whereas the vertical lines with y-scale magnitude "2" imply the predicted HRflex values calculated as the mean of maximal HR during rest and minimal HR during exercises.

The representative data of FIG. 3 illustrates that the basal HR and HRflex values are highly variable among the plurality of sample subjects and cannot distinctively separate the basal and active periods with respect to HR. Thus, the previous art of determining HRflex point as a function of instantaneous HR is highly variable and moreover unreliable because the calibrated HRflex values can be lower than their basal HR as shown in FIG. 3. Inaccurate prediction of HRflex point in previous methods may result in utilizing the wrong choice of EE prediction models for basal and active states that may lead to significant errors in EE rate. This is the reason why the periodic calibration procedures are very necessary for each individual in order to provide reasonable estimates of energy expenditure.

Figure 4:
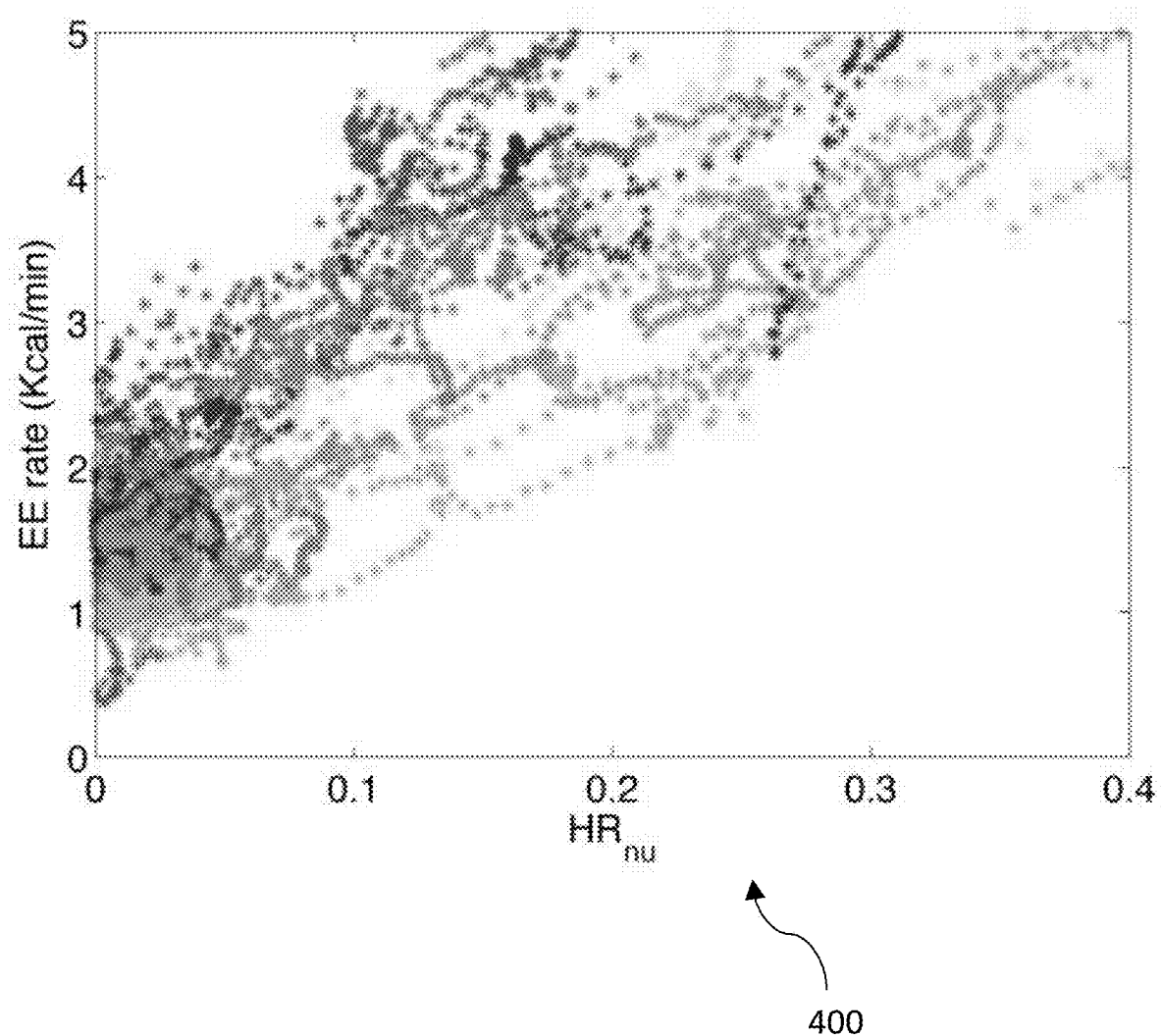
FIG. 4 illustrates a diagram of the relationship between energy expenditure (EE) rate and normalized heart rate ($HR_{nu}$) in accordance with an embodiment.

On the other hand, FIG. 4 illustrates a diagram 400 of the relationship between energy expenditure (EE) rate (in Kcal/min) and normalized heart rate ($HR_{nu}$) values in accordance with an embodiment. In one embodiment, the $HR_{nu}$ threshold (or break point) that separates resting to active states is learned and/or adjusted from training data (e.g. clinical trial data) and in another embodiment, the $HR_{nu}$ threshold is predetermined and automatically and continuously updated using cloud-stored data from the same users. If the basic resting bodily functions like breathing, blood circulation, and metabolism represent no more than 10% of an individual's $HR_{nu}$ (e.g., $HR_{nu}$=0.1), the resting and active states are very clearly separated among the plurality of sample subjects, as shown in FIG. 4.

In one embodiment, the wearable device determines the energy expenditure (EE) rate of the user by utilizing a first algorithmic process to split the HR spectrum into two or more linear regression models. The first algorithmic process comprises a piecewise linear regression model with one break point (PLR_ob). In one embodiment, the break point is determined as a fraction of the user's heart rate reserve (HRR). In one embodiment, the break point is learned and/or adjusted from training data (e.g. clinical trial data) and in another embodiment, the break point is predetermined and automatically and continuously updated using cloud-stored data from the same user or a population of users.

Figure 5:
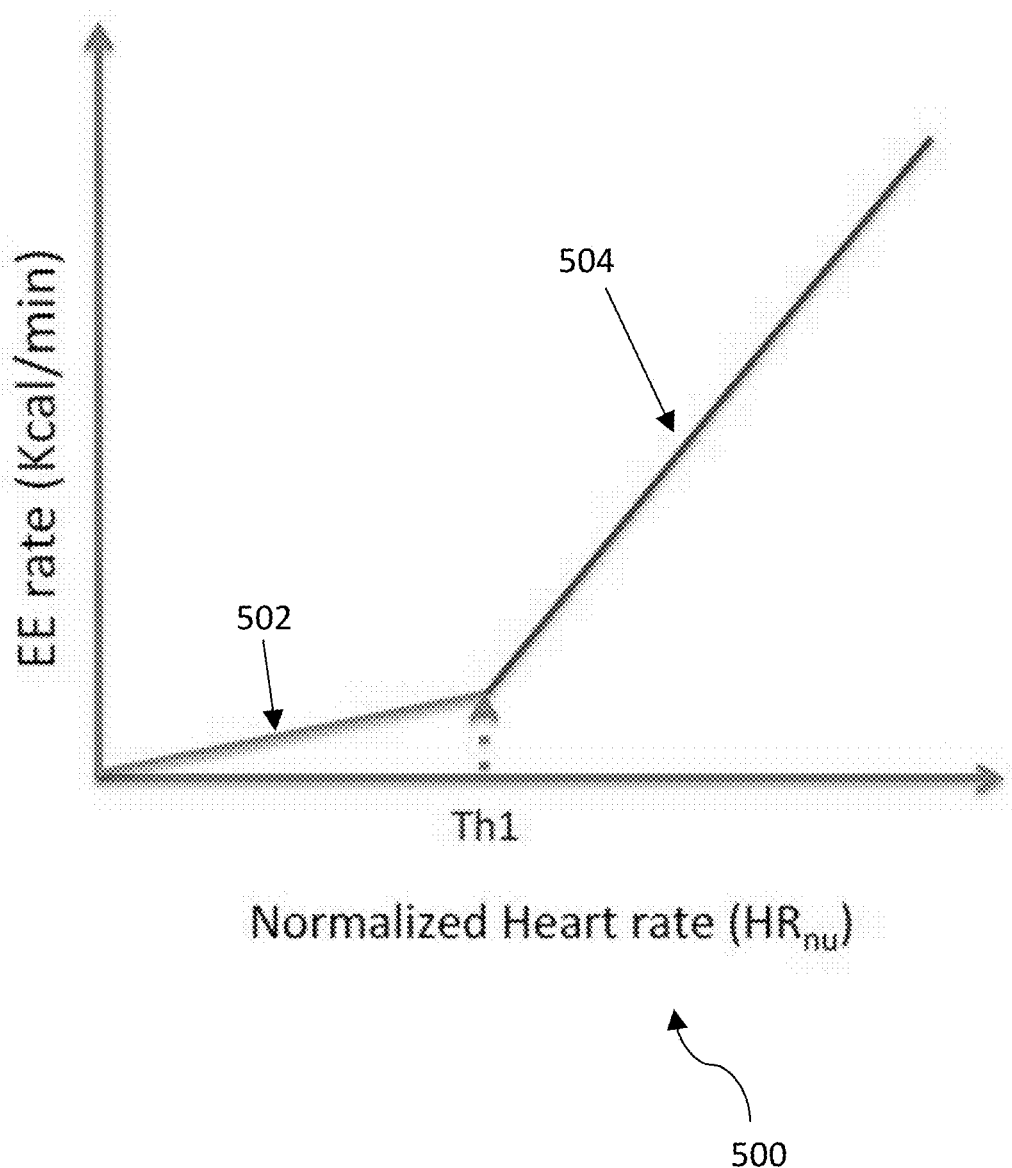
FIG. 5 illustrates a diagram of a piecewise linear regression model with one break point in accordance with a first embodiment.

FIG. 5 illustrates a diagram of a piecewise linear regression model 500 with one break point in accordance with a first embodiment. The piecewise linear regression model 500 is plotted between a normalized heart rate ($HR_{nu}$) and an EE rate in Kcal/min. The cut-off point/threshold (Th1) of normalized HR ($HR_{nu}$) splits the range of $HR_{nu}$ into two separate zones of basal and active states with two independent linear regression models 502-504, respectively. Based on the input values of $HR_{nu}$, the appropriate prediction model will be applied to the input feature vector and the EE rate values will be predicted. In one embodiment, the threshold Th1 is learned and/or adjusted from training data (e.g. clinical trial data) and in another embodiment, the threshold is predetermined and automatically and continuously updated using cloud-stored data from the same user or a population of users.

As a result, the two independent linear regression models 502-504 are learned by the machine learning module of the wireless sensor device 100 (or external relay device) to predict the corresponding EE rate with respect to the changes in the $HR_{nu}$ values. The piecewise linear regression model 500 enables the prediction/determination of the EE rate separately for two different zones/types of activity including but not limited to resting and an active state. In one embodiment, each of the two independent linear regression models 502-504 are defined per the following equation:

$$y(x, w) = w_0 + \sum_{j=1}^{M-1} w_j x = w^T x; \quad \text{(Equation 1)}$$

where, x is the input feature space $x=(x_1, \ldots, x_D)^T$, w is the model parameters $w=(w_0, \ldots, x_{M-1})^T$, and y is the predicted output. Therefore, the piecewise linear regression model 500 does not require any calibration procedures (such as the HRFlex method) to determine the break/flex point that changes the model parameters.

Figure 6:
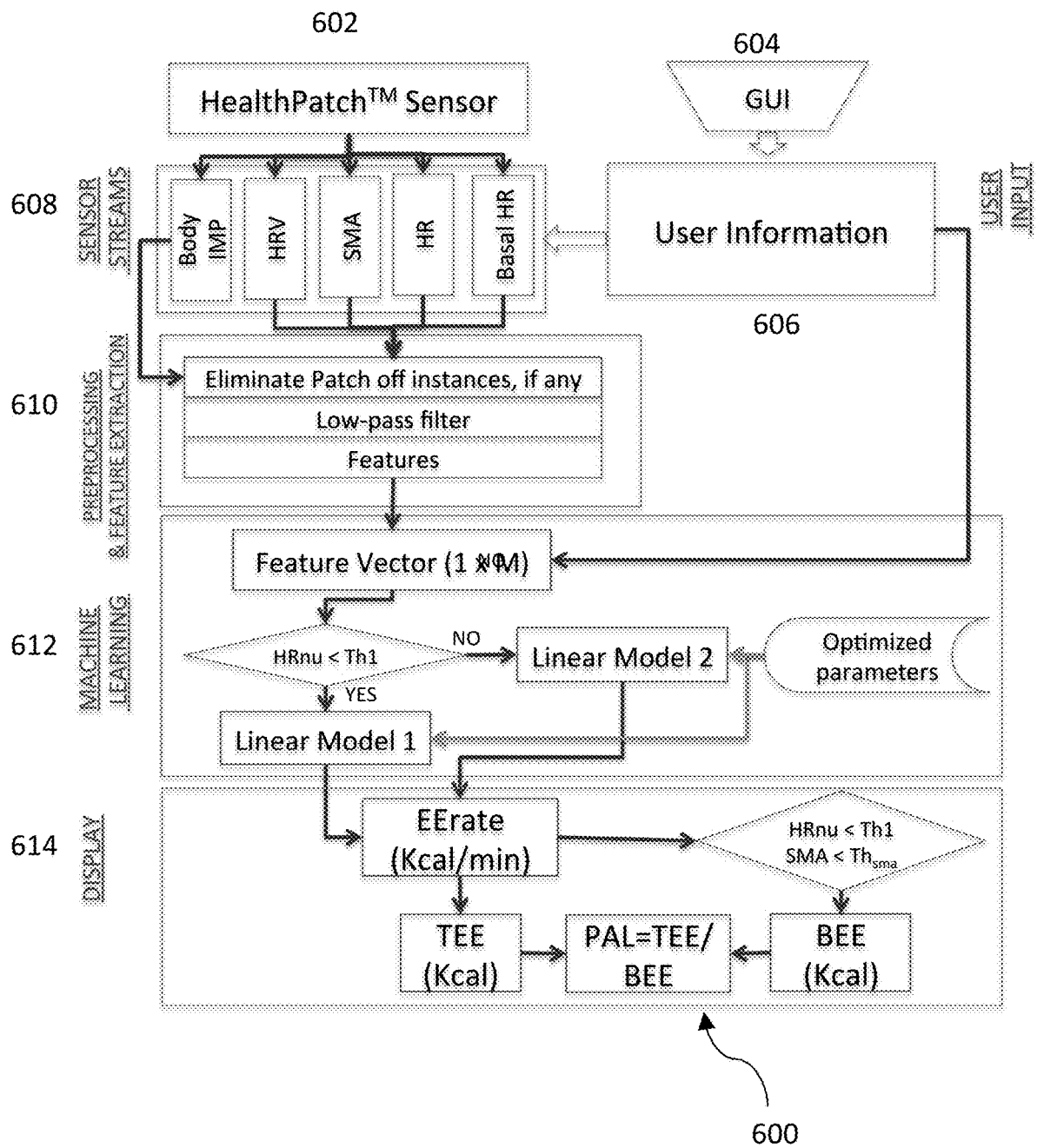
FIG. 6 illustrates a detailed flow chart of a system for determining energy expenditure (EE) in accordance with a first embodiment.

FIG. 6 illustrates a detailed flow chart of a system 600 for determining energy expenditure (EE) in accordance with a first embodiment. The system 600 utilizes the piecewise linear regression model 500 and does not require calibration procedures for the selection of the break point. The system 600 includes a wearable device 602 with an embedded detection module, a graphical user interface (GUI) module (604) that allows input of user specific information including and not limited to height, weight, age, and gender, a user information module 606, a sensor streams module 608, a feature extraction module 610, a machine learning module 612, and a display module 614. In one embodiment, each of the components (608 to 614) of the system 600 is coupled serially. In one embodiment, the embedded detection module comprises a plurality of sensors for detecting various physiological signals of the user (e.g. heart rate, acceleration signals, etc) that are then converted into sensor streams by the sensor streams module 608. In one embodiment, the wearable device 602 is a HealthPatch™ wearable device.

In one embodiment, the sensor streams module 608, the feature extraction module 610, the machine learning module 612, and the display module 614 are all incorporated into an external relay device/processor including but not limited to a smartphone, a wall unit relay, and a cloud processor. In one embodiment, the aforementioned modules 608-614 are each stand-alone devices that are coupled to and in communication with the wearable device 602. In another embodiment, the wearable device 602 incorporates the aforementioned modules 608-614 into a singular wearable sensor device.

In one embodiment, the user information module 606 comprises patient demographic information that is either user/patient or doctor submitted via a graphical user interface (e.g. on the wireless device 602 or the relay device such as a smartphone) and includes but is not limited to age, weight, height, gender, and medical history information; the sensor streams module 608 determines a plurality of sensor streams including but not limited to body impedance, heart rate variability (HRV), signal magnitude area (SMA), heart rate (HR), and basal HR; the feature extraction module 610 includes a preprocessing module that eliminates patch off instances (if any) and that utilizes a low pass filter to eliminate noise from the plurality of sensor streams, and then extracts various features from the plurality of sensor streams to derive a feature vector (Fv) based upon the extracted features and the patient demographic information; the machine learning module 612 utilizes the feature vector Fv (for example, the size of Fv=1×M) to determine whether $HR_{nu}$ is less than or greater than the break point Th1.

If $HR_{nu}$ is less than the threshold Th1 ($HR_{nu}$<Th1), a first linear model that corresponds to the resting/basal state is used to predict EE rate accordingly. Otherwise, if $HR_{nu}$ is greater than or equal to the threshold Th1 (e.g., $HR_{nu} \geq$ Th1), a second linear model that corresponds to the active state is used to predict the EE rate. The parameters of these two linear models are optimized from the clinical trials. A continuous stream of the energy expenditure (EE) rate in Kcal/min is predicted using the optimized linear regression models based on the feature vector and $HR_{nu}$; and the display module 614 outputs the EE rate of the user as well as other EE associated values of the user including but not limited to total daily expenditure (TEE) in Kcal, basal energy expenditure (BEE) in Kcal, and a physical activity level (PAL).

The total energy expenditure (TEE) is obtained as the integration of EE rate over a predetermined time period (for example, exercise period that may last minutes to hours or a 24 hour time period). The basal energy expenditure value is obtained by the integration of samples of EE rates that satisfy two conditions: (i) $HR_{nu}$<Th1 and (ii) the signal magnitude area (SMA) of accelerometer signals less than a predefined SMA threshold $Th_{sma}$ (SMA<$Th_{sma}$). When these two conditions are satisfied, it implies that the subject is under resting or basal state. The accumulation of EE rates under only the basal state provides the estimate of basal energy expenditure (BEE). The physical activity level (PAL) is a numerical representation of an individual's activity level and is quantified as the ratio of TEE and BEE. PAL helps to indicate whether the life style is inactive, sedentary, moderately active, vigorously active or extremely active.

Figure 7:
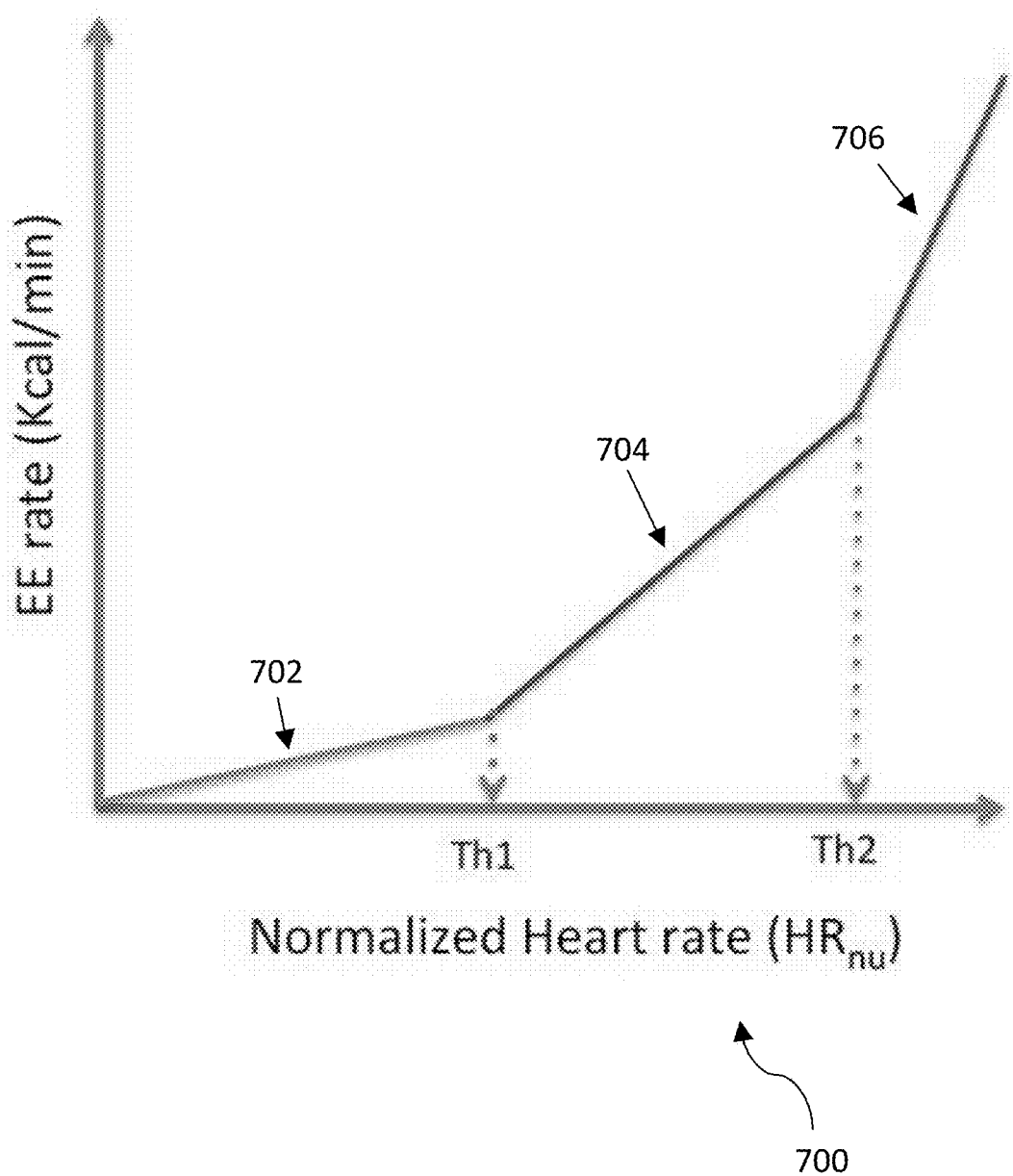
FIG. 7 illustrates a diagram of a piecewise linear regression model with two break points in accordance with a second embodiment.

FIG. 7 illustrates a diagram of a piecewise linear regression model 700 with two break points in accordance with a second embodiment. The piecewise linear regression model 700 is plotted between a normalized heart rate ($HR_{nu}$) and an EE rate in Kcal/min. The piecewise linear regression model 700 predicts the EE rate using three separate linear regression models 702-704-706 based on the input $HR_{nu}$. The boundaries of the $HR_{nu}$ thresholds (Th1 and Th2) that serve as two break points determine which prediction model is to be used to compute EE rate. In one embodiment, the thresholds Th1 and Th2 are learned and/or adjusted from training data (e.g. clinical trial data) and in another embodiment, the thresholds are predetermined and automatically and continuously updated using cloud-stored data from the same user or a population of users.

As a result, the three separate linear regression models 702-704-706 are learned by the machine learning module of the wireless sensor device 100 (or external relay device) to predict the corresponding EE rate with respect to the changes in the $HR_{nu}$ values. The piecewise linear regression model 700 enables the prediction/determination of the EE rate separately for three different zones of activity including but not limited to resting, low-to-moderate intensity activities, and high-intensity activities. In one embodiment, each of the three linear regression models 702-704-706 are defined per the aforementioned Equation 1 and as follows:

$$y(x, w) = w_0 + \sum_{j=1}^{M-1} w_j x = w^T x; \quad \text{(Equation 1)}$$

where, x is the input feature space $x=(x_1, \ldots, x_D)^T$, w is the model parameters $w=(w_0, \ldots, x_{M-1})^T$, and y is the predicted output. Therefore, the piecewise linear regression model 700 does not require any calibration procedures (such as the HRflex method) to determine the break points that changes the model parameters.

Figure 8:
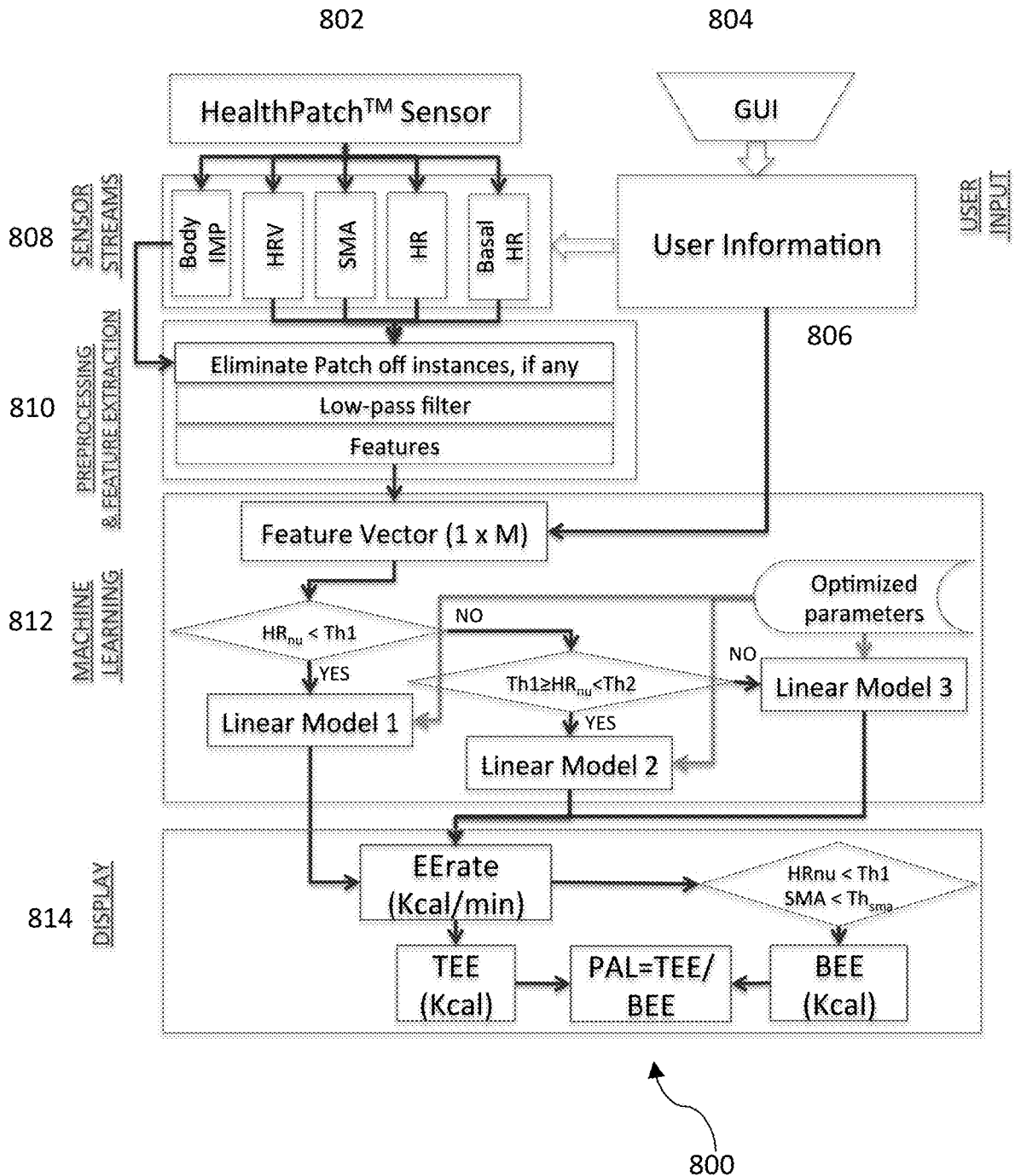
FIG. 8 illustrates a detailed flow chart of a system for determining energy expenditure (EE) in accordance with a second embodiment.

FIG. 8 illustrates a detailed flow chart of a system 800 for determining energy expenditure (EE) in accordance with a second embodiment. The system 800 includes a wearable device 802 with an embedded detection module, a graphical user interface (GUI) module (804) that allows input of user specific information including and not limited to height, weight, age, and gender, a user information module 806, a sensor streams module 808, a feature extraction module 810, a machine learning module 812, and a display module 814. In one embodiment, each of the components (808 to 814) of the system 800 is coupled serially. In one embodiment, the embedded detection module comprises a plurality of sensors for detecting various physiological signals of the user (e.g. heart rate, acceleration signals, etc) that are then converted into sensor streams by the sensor streams module 808. In one embodiment, the wearable device 802 is a HealthPatch™ wearable device.

In one embodiment, the user information module 804, the sensor streams module 808, the feature extraction module 810, the machine learning module 812, and the display module 814 are all incorporated into an external relay device/processor including but not limited to a smartphone, a wall unit relay, and a cloud processor. In one embodiment, the aforementioned modules 808-814 are each stand-alone devices that are coupled to and in communication with the wearable device 802. In another embodiment, the wearable device 802 incorporates the aforementioned modules 808-814 into a singular wearable sensor device.

In one embodiment, the user information module 806 comprises patient demographic information that is either user/patient or doctor submitted via the graphical user interface 804 and includes but is not limited to age, weight, height, gender, and medical history information; the sensor streams module 808 determines a plurality of sensor streams including but not limited to body impedance, heart rate variability (HRV), signal magnitude area (SMA), heart rate (HR), and basal HR; the feature extraction module 810 includes a preprocessing module that eliminates patch off instances (if any) and that utilizes a low pass filter to eliminate noise from the plurality of sensor streams, and then extracts various features from the plurality of sensor streams to derive a feature vector (Fv) based upon the extracted features and the patient demographic information; the machine learning module 812 applies the feature vector Fv (for example, the size of Fv=1×M) to a linear regression model to predict the EE rates. The applied linear regression model is determined based on the value of normalized heart rate ($HR_{nu}$).

When the $HR_{nu}$ is less than the threshold Th1 ($HR_{nu}$<Th1), a first linear regression model that corresponds to a resting (or basal) state is used for the prediction of the EE rate. If the $HR_{nu}$ is greater than or equal to Th1 and also less than Th2 (Th1≤$HR_{nu}$<Th2), then a second linear regression model that corresponds to a state of low-to-moderate intensity activities is used for the prediction of the EE rate. If $HR_{nu}$ is greater than or equal to Th2 ($HR_{nu}$≥Th2), then a third linear regression model that corresponds to a state of intense activities is used for the prediction of the EE rate.

These three separate linear regression models are trained and optimized using clinical trial data. Based on the values of $HR_{nu}$, feature vector and the selection of linear regression model and their optimized model parameters, the energy expenditure (EE) rate values are predicted in Kcal/min; and the display module 814 outputs the EE rate of the user as well as other EE associated values of the user including but not limited to total daily expenditure (TEE) in Kcal, basal energy expenditure (BEE) in Kcal, and a physical activity level (PAL).

The total energy expenditure (TEE) is obtained as the integration of EE rate over a predetermined time period (for example, exercise period that may last minutes to hours or a 24 hour time period). The basal energy expenditure value is obtained by the integration of samples of EE rates that satisfy two conditions: (i). $HR_{nu}$<Th1 and (ii) the signal magnitude area (SMA) of accelerometer signals less than a predefined SMA threshold $Th_{sma}$ (SMA<$Th_{sma}$). When these two conditions are satisfied, it implies that the subject is under resting or basal state. The accumulation of EE rates under only the basal state provides the estimate of basal energy expenditure (BEE). The physical activity level (PAL) is a numerical representation of an individual's activity level and is quantified as the ratio of TEE and BEE. PAL helps to indicate whether the life style is inactive, sedentary, moderately active, vigorously active or extremely active.

Figure 9:
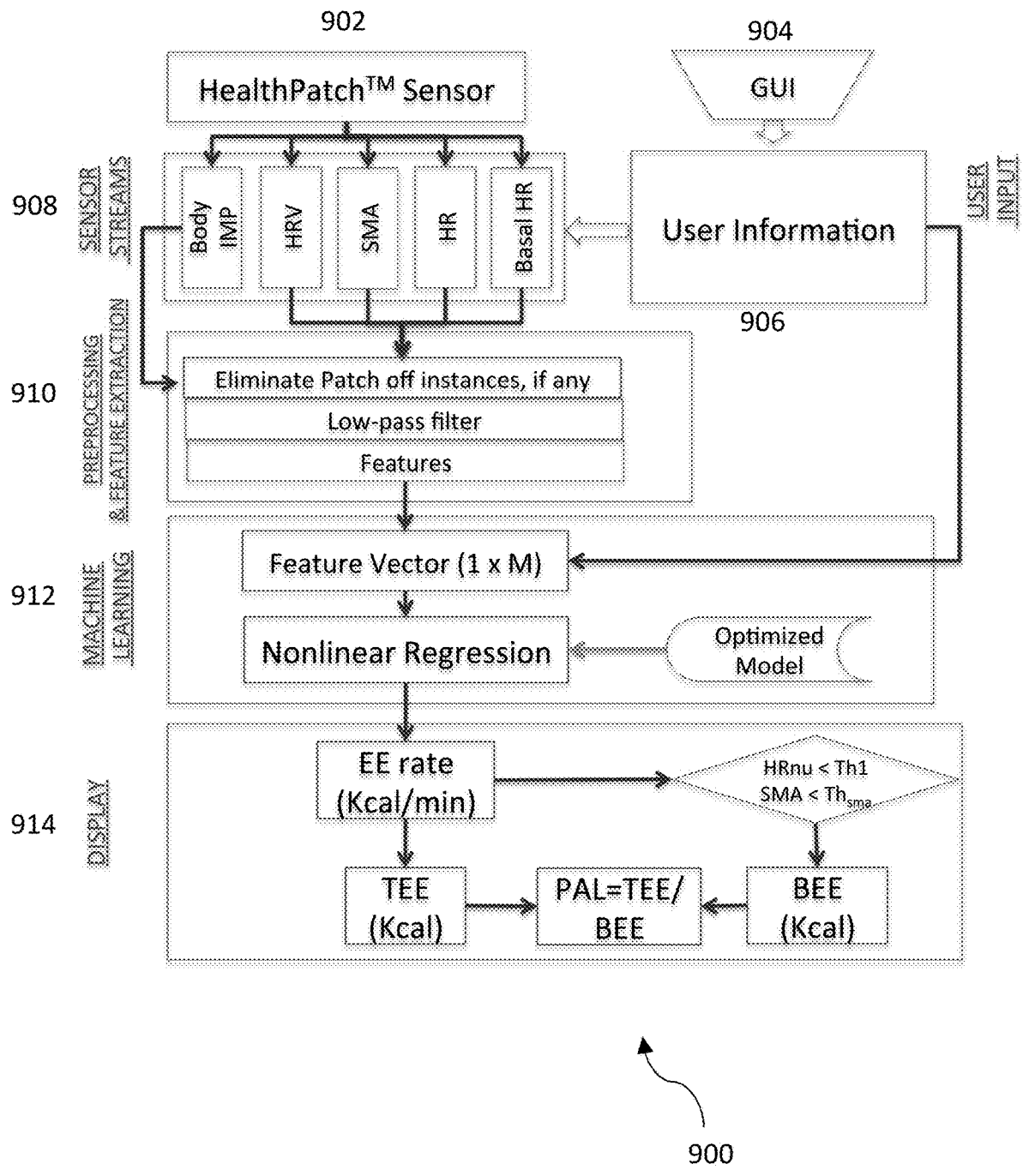
FIG. 9 illustrates a detailed flow chart of a system for determining energy expenditure (EE) using nonlinear regression in accordance with a third embodiment.

In a third embodiment, the EE rate of the user can be predicted using a method and a system that assumes the relationship between the EE rate and the heart rate/activity of the user as nonlinear. FIG. 9 illustrates a detailed flow chart of a system 900 for determining energy expenditure (EE) using nonlinear regression in accordance with an embodiment. The system 900 includes a wearable device 902 with an embedded detection module, a graphical user interface (GUI) module (904) that allows input of user specific information including and not limited to height, weight, age, and gender, a user information module 906, a sensor streams module 908, a feature extraction module 910, a machine learning module 912, and a display module 914. In one embodiment, each of the components (908 to 914) of the system 900 is coupled serially. In one embodiment, the embedded detection module comprises a plurality of sensors for detecting various physiological signals of the user (e.g. heart rate, acceleration signals, etc) that are then converted into sensor streams by the sensor streams module 908. In one embodiment, the wearable device 902 is a HealthPatch™ wearable device.

In one embodiment, the user information module 906, the sensor streams module 908, the feature extraction module 910, the machine learning module 912, and the display module 914 are all incorporated into an external relay device/processor including but not limited to a smartphone, a wall unit relay, and a cloud processor. In one embodiment, the aforementioned modules 908-914 are each stand-alone devices that are coupled to and in communication with the wearable device 902. In another embodiment, the wearable device 902 incorporates the aforementioned modules 908-914 into a singular wearable sensor device.

In one embodiment, the user information module 906 comprises patient demographic information that is either user/patient or doctor submitted via the graphical interface unit 904 and includes but is not limited to age, weight, height, gender, and medical history information; the sensor streams module 908 determines a plurality of sensor streams including but not limited to body impedance, heart rate variability (HRV), signal magnitude area (SMA), heart rate (HR), and basal HR; the feature extraction module 910 includes a preprocessing module that eliminates patch off instances (if any) and that utilizes a low pass filter to eliminate noise from the plurality of sensor streams, and then extracts various features from the plurality of sensor streams to derive a feature vector (Fv) based upon the extracted features and the patient demographic information; the machine learning module 912 utilizes the feature vector Fv (for example, the size of Fv=1×M) and nonlinear regression analysis based upon an optimized model to determine the energy expenditure (EE) rate in Kcal/min; and the display module 914 outputs the EE rate of the user as well as other EE associated values of the user including but not limited to total daily expenditure (TEE) in Kcal, basal energy expenditure (BEE) in Kcal, and a physical activity level (PAL).

The total energy expenditure (TEE) is obtained as the integration of EE rate over a predetermined time period (for example, exercise period that may last minutes to hours or a 24 hour time period). The basal energy expenditure value is obtained by the integration of samples of EE rates that satisfy two conditions: (i). $HR_{nu}$<Th1 and (ii) the signal magnitude area (SMA) of accelerometer signals less than a predefined SMA threshold $Th_{sma}$ (SMA<$Th_{sma}$). When these two conditions are satisfied, it implies that the subject is under resting or basal state. The accumulation of EE rates under only the basal state provides the estimate of basal energy expenditure (BEE). The physical activity level (PAL) is a numerical representation of an individual's activity level and is quantified as the ratio of TEE and BEE. PAL helps to indicate whether the life style is inactive, sedentary, moderately active, vigorously active or extremely active.

The system 900 assumes the relationship between the EE rate and the heart rate/activity of the user as nonlinear and learns a nonlinear regression model using clinical trial data. In one embodiment, the nonlinear prediction model is defined per the following equation:

$$y(x, w) = \sum_{j=1}^{M-1} w_j \phi_j(x) = w^T \phi(x); \quad \text{(Equation 2)}$$

where, $\phi(x)$ is the basis function that can include and not limited to quadratic polynomial, higher order polynomial, exponential function, radial basis function, and sigmoidal function. Therefore, the nonlinear prediction model utilized by the system 900 does not involve determining/predicting any break points and thus does not require any calibration procedures (such as the HRflex method) to determine the break points that change the model parameters.

The first, second and third embodiments represented by 600, 800, and 900 respectively, all have common modules (e.g., GUI, sensor streams module, user information module, feature extraction module, display module) except the machine learning module. The aforementioned system 600 consists of one break point as a fraction of $HR_{nu}$, that splits the determination/prediction of the EE rate of the user into two separate linear regression problems representing basal and active states. On the other hand, the aforementioned system 800 consists of two break points as different fractions of $HR_{nu}$ that splits the determination/prediction of the EE rate of the user into three separate linear regression problems representing basal, low-to-moderate intensity activity and high-intensity activity states. The first two embodiments operate under the assumption that the relationship between heart rate/activity and the rate of energy expenditure is linear for a given boundaries of normalized heart rate ($HR_{nu}$). On the other hand, the third embodiment represented by the system 900 assumes that the relationship between heart rate/activity and the rate of energy expenditure is a nonlinear function independent of the states of resting or various levels of activities represented by the normalized hear rate ($HR_{nu}$). The training and optimization of these prediction models are carried out using clinical trials.

Sensor Streams Modules:

The aforementioned sensor streams modules 608-808-908 each analyze the physiological signal data that has been detected by the embedded detection module of the wearable device (602, 802, and 902 respectively) to derive a plurality of sensor streams. Each sensor streams module records the plurality of sensor streams for a predetermined time period including but not limited to seconds, minutes, hours, overnight, days, weeks, months, and years. Each sensor streams module stores the plurality of sensor streams on a memory device of the wearable device at either real-time or near real-time. In one embodiment, the plurality of sensor streams include body impedance, SMA, HRV, HR, and basal HR ($HR_b$).

In one embodiment, the sensor streams derived from an ECG signal detected by the wearable device on a beat-to-beat basis include but are not limited to heart rate variability (HRV), HR, $HR_b$, QRS wave amplitude (RWA), and QRS wave area (RA). RWA and RA are defined as the range of ECG voltages and the absolute/signed area under the ECG signal, respectively, within a window of 100 milliseconds (ms) centered at the QRS peak of each beat. The sensor streams derived from tri-axial acceleration signals include but are not limited to MEMS-based respiration signals ($RESP_{MEMS}$), signal magnitude area (SMA) as an activity metric, and polar angles of posture.

In one embodiment, the wearable device 602-802-902 also measures a body impedance value in between the two electrodes. In one embodiment, ECG derived signals are recorded on a beat-to-eat basis; SMA, posture angles and body impedance signals are sampled at a predetermined time period including but not limited to 4 seconds; and $RESP_{MEMS}$ signal is uniformly sampled at a predetermined frequency including but not limited to 4 Hz. In another embodiment, the SMA, posture angles and body impedance signals are sampled every predetermined seconds including but not limited to predetermined ranges within 1 to 60 seconds.

Feature Extraction Modules:

The aforementioned feature extraction modules 610-810-910 each receive the sensor streams from the respective sensor streams modules 608-808-908 (or stand-alone preprocessing module) and extract a plurality of features. In one embodiment, the system 600-800-900 further includes a stand-alone preprocessing module that processes the plurality of sensor streams that have been derived by each sensor streams module before they are transmitted by the sensor streams module to the feature extraction module.

In another embodiment, each feature extraction module includes the preprocessing module. In one embodiment, the preprocessing module eliminates patch off instances using body impedance values detected by the wearable device, normalizes the sensor streams, for example a normalized HR series as a function of basal HR ($HR_b$), and filtering the sensor streams. The filtering process includes but not limited to a low pass filter.

After the preprocessing of the sensor streams, each feature extraction module derives physiological features from the low-pass filtered/preprocessed sensor streams and then determines a feature vector (Fv) that consists of the derived physiological features and inputted user information from the user information module. In one embodiment, the feature vector (Fv) includes but is not limiting to user (patient) information and related features (including but not limited to height, weight, gender, age), HR related features (including but not limited to HR, normalized HR, HRV, basal HR), and activity related features (including but not limited to signal magnitude area SMA).

Machine Learning Modules:

The aforementioned machine learning modules 612-812-912 each receive the determined feature vector (Fv) from the output of the respective feature extraction modules 610-810-910 and then utilizes the received feature vector (Fv), a plurality of machine learning regression models to predict the energy expenditure (EE) rate and other EE related parameters of the user including but not limited to total daily energy expenditure (TEE), basal energy expenditure (BEE), and a physical activity level (PAL) of the user. The BEE values are calculated based upon the instantaneous EE rates obtained from each machine-learning module for only the inactive resting state determined using the sensor streams of $HR_{nu}$ and SMA compared to their respective thresholds of $HR_{nu}$ and SMA. The linear regression models (linear model 1, linear model 2, linear 3) utilized by the system 500 (utilizes only linear model 1 and linear model 2) and by system 700 (utilizes all three linear models 1, 2, and 3) are all represented by the aforementioned Equation 1. The nonlinear regression model is utilized by system 900 and is represented by the aforementioned Equation 2.

In one embodiment, the regression models are obtained by each machine learning module using a variety of regression analysis tools including but not limited to ordinary least squares, generalized least squares, ridge regression, lasso, and support vector regression. The aforementioned display modules 614-814-914 (that are either integrated into the wearable device itself or a relay device such as a smartphone) each output the derived EE rate in Kcal/min as well as the other EE related metrics (TEE, BEE, and PEE) to the user/doctor for viewing/storage/analysis.

The optimal parameters of the regression analysis are determined by an optimization process involved with leave-one-out cross validation and minimizing the mean square error of the predicted EE rate values by adjusting the parameter values (for example, the cost function C in case of linear support vector regression analysis). Then, the optimized regression model coefficients w are obtained by fitting the regression model with optimal regression parameters using all the training data sets.

Figure 10:
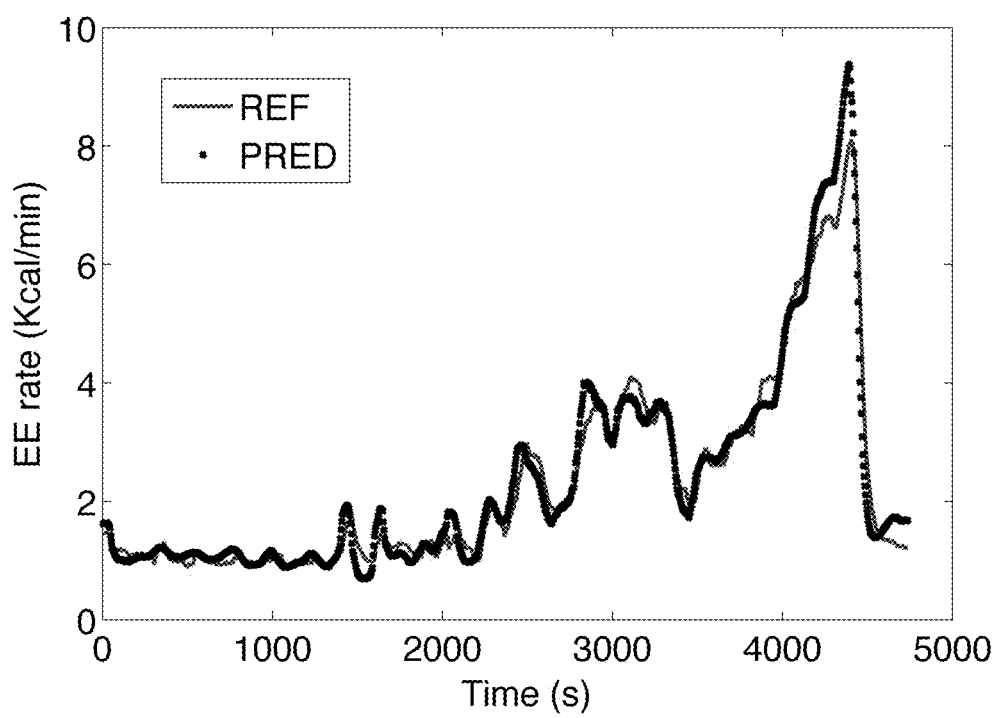
FIG. 10 illustrates a diagram that compares the predicted energy expenditure (EE) rate determinations to the reference values in accordance with an embodiment.

FIG. 10 illustrates a diagram 1000 that compares the predicted energy expenditure (EE) rates with the reference values in accordance with an embodiment. The references values are reference EE rates as a function of time in x axis. In FIG. 10, the predicted EE rates show great correspondence to that of the reference EE rates through distinct states of basal, low, moderate and intense activity periods followed by the recovery period. The diagram 1000 shows a close correlation between the reference EE rate values and the predicted EE rate values by a method and system in accordance with the present invention. This data indicates that the present invention provides very accurate prediction of EE rates.

Figure 11:
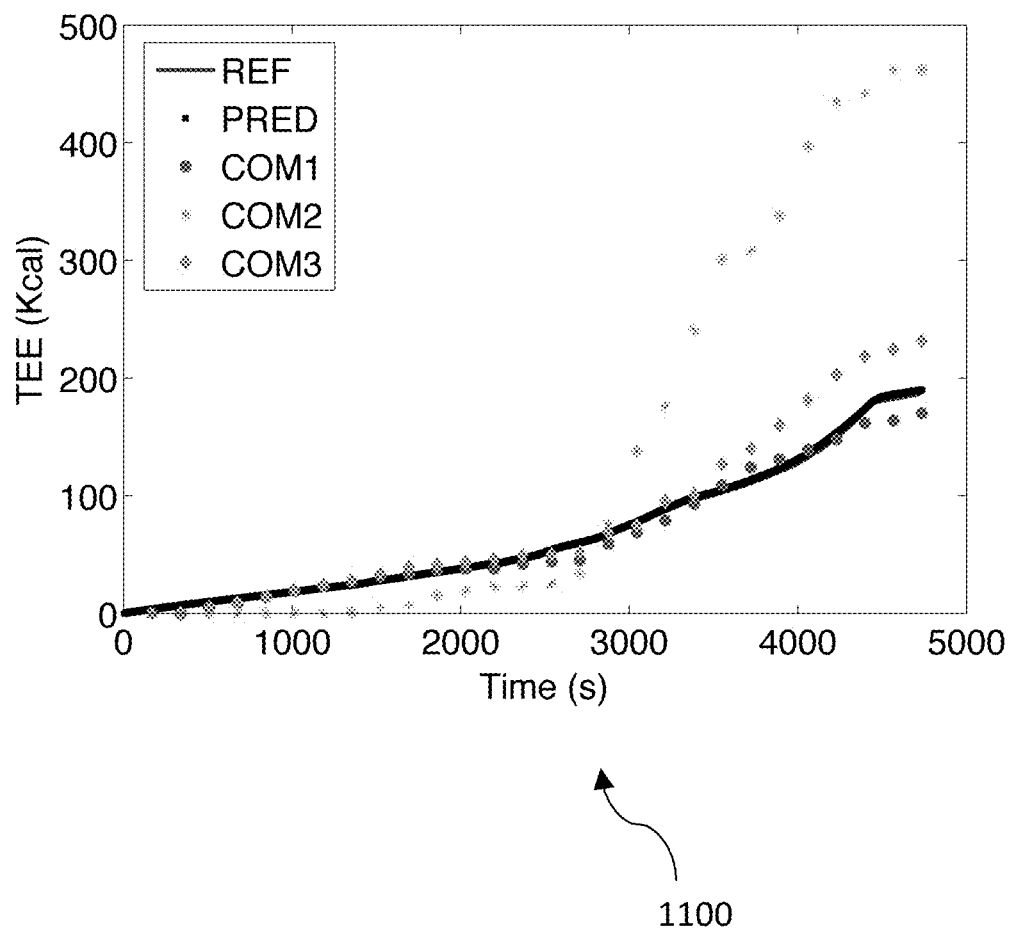
FIG. 11 illustrates a diagram that compares the predicted total energy expenditure determinations to the reference values in accordance with an embodiment.

The system and method of the present invention provides the time series of cumulative changes on total energy expenditure (TEE) based on the predicted EE rates. FIG. 11 illustrates a diagram 1100 that compares the predicted total energy expenditure determinations to the reference values in accordance with an embodiment. The references values are reference TEE values and TEE measurements from 3 commercially available devices (COM1, COM2 and COM3). The incremental changes in the predicted TEE followed the reference TEE estimates over time very closely through distinct states of basal, low, moderate and intense activity periods followed by the recovery period. The TEE value is determined both by an accurate reference method (Ref) and by a method and system in accordance with the present invention (Pred) and shows a close correlation between the two determinations. On the other hand, the commercial devices are shown to produce under estimation of TEE during resting and over estimation during active periods. Therefore, the present invention is able to provide most accurate estimates of the TEE.

In one embodiment, the wearable device is disposable, inexpensive, unobtrusive, simple to attach, and easy to connect/pair wirelessly with external devices including but not limited to the user/patient's smartphone. The physiological and sensor stream data is encrypted and transmitted via a BLE link to external relay processor (e.g., smartphone) for further processing to automatically and continuously determine the energy expenditure (EE) values (e.g. EE rate) and related determinations which are then stored for further analysis and viewing. The predicted/determined EE values are displayed on the smartphone application screen/computer screen. From the smartphone/server, an analysis report is produced that can be easily sent to a physician or a family member.

As above described, a method and system in accordance with the present invention utilizes a wearable device (e.g., HealthPatch™ patch sensor) to determine a plurality of energy expenditure (EE) values of a user. By utilizing wearable devices to detect a plurality of physiological signals (e.g., ECG signal and acceleration signals) via a plurality of embedded sensors (e.g., ECG sensor, a MEMS accelerometer, and derived sensors), and utilizing a processor (e.g., any of an embedded electronic module/processor in the wearable device, an external relay/cloud processor such as a smartphone device, and a cloud computing system) to perform preprocessing, user inputting, feature extraction, machine learning, and regression model analytics, the method and system in accordance with the present invention continuously and automatically determines the EE values of the user based upon a combination of the heart rate (HR) and activity/acceleration signal values.

The method and system in accordance with the present invention does not require any calibration procedures because the one or more break points utilized by the aforementioned systems 600 and 800 are obtained as a function of normalized heart rate ($HR_{nu}$) instead of merely a function of heart rate. The thresholds of $HR_{nu}$ that serve as the one or more break points are predetermined (e.g., from a clinical trial). These thresholds are easily generalized as shown in FIG. 4, since the $HR_{nu}$ is a normalized quantity that does not vary so much across populations. In addition, the method and system in accordance with the present invention utilizes a wearable device to accurately and continuously monitor a user's heart rate (HR) and detect body acceleration signals from the user's torso instead of merely detecting acceleration signals from extremities/pockets of clothing which are less accurate.

A method and system for determining energy expenditure (EE) has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or calculator-readable medium. The software application provides instructions that enable the processor to perform the functions described herein.

Furthermore, embodiments may take the form of a calculator program product accessible from a calculator-usable or calculator-readable medium providing program code for use by or in connection with a calculator or any instruction execution system. For the purposes of this description, a calculator-usable or calculator-readable medium can be any apparatus that can contain, store, communicate, propagate, or transport the program for use by or in connection with the instruction execution system, apparatus, or device.

The medium may be an electronic, magnetic, optical, electromagnetic, infrared, semiconductor system (or apparatus or device), or a propagation medium. Examples of a calculator-readable medium include a semiconductor or solid state memory, magnetic tape, a removable calculator diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for determining energy expenditure (EE) of a user/patient, the method comprising:
   detecting a plurality of physiological signals using a wearable sensor device, wherein the plurality of detected physiological signals are detected by a wearable device and include any of an electrocardiogram (ECG) signal and an acceleration signal;
   converting the plurality of physiological signals into a plurality of sensor streams, wherein the plurality of sensor streams include any of body impedance, heart rate (HR), basal heart rate ($HR_b$), heart rate variability (HRV), and signal magnitude area (SMA);
   a preprocessing step for eliminating wearable device off instances using body impedance values;
   extracting features from each of the plurality of sensor streams, and determining a feature vector using extracted features and demographic information of the user/patient; and
   determining the EE by performing machine learning using the determined feature vector and a regression model, wherein the regression model corresponding to a specific activity state is selected based on value of normalized heart rate ($HR_{nu}$).

2. The method of claim 1, wherein the processing step is performed by any of a wearable device, an external device, a relay/cloud processor, a smartphone device, and a cloud computing system.

3. The method of claim 1, wherein the preprocessing step further comprises any of:
   low-pass filtering the plurality of sensor streams; and normalizing the plurality of sensor streams, and
   normalizing the plurality of sensor streams, wherein the normalized heart rate ($HR_{nu}$) is determined as any of a function of basal heart rate ($HR_b$), a function of maximal allowable heart rate ($HR_{max}$), and a fraction of heart rate reserve (HRR).

4. The method of claim 1, wherein the feature vector includes user/patient information related features that include any of height, weight, gender, age; heart rate related features that include any of heart rate (HR), normalized heart rate, and heart rate variability (HRV); and activity features that include signal magnitude area (SMA).

5. The method of claim 1, wherein the regression model is a piecewise linear regression model with a break point, wherein the break point is a function of a normalized heart rate ($HR_{nu}$) and is determined as a fraction of heart rate reserve (HRR), wherein the break point splits the determination of the EE into two separate linear regressions.

6. The method of claim 1, wherein the regression model is a piecewise linear regression model with two break points, wherein the two break points are a function of a normalized heart rate ($HR_{nu}$) and are each determined as a fraction of heart rate reserve (HRR), wherein the two break points split the determination of the EE into three separate linear regressions.

7. The method of claim 1, wherein the regression model is a nonlinear regression that does not include a break point.

8. The method of claim 1, wherein to determine the EE comprises the determination of any of an energy expenditure (EE) rate, total daily energy expenditure (TEE), basal energy expenditure (BEE), and a physical activity level (PAL) as the ratio of TEE/BEE.

9. A system for determining energy expenditure (EE) of a user/patient, the system comprising at least one sensor to detect a plurality of physiological signals, a processor coupled to the at least one sensor, and a memory device coupled to the processor, wherein the memory device includes an application that, when executed by the processor, causes the processor to:

convert the plurality of physiological signals detected using the sensor into a plurality of sensor streams, wherein the plurality of physiological signals include any of an electrocardiogram (ECG) signal and an acceleration signal and wherein the plurality of sensor streams include any of body impedance, heart rate (HR), basal heart rate ($HR_b$), heart rate variability (HRV), and signal magnitude area (SMA);

extract features from each of the plurality of sensor streams, and determine a feature vector using extracted features and demographic information of the user/patient; and determine the EE by performing machine learning using the determined feature vector and a regression model, wherein the regression model corresponding to a specific activity state is selected based on value of normalized heart rate ($HR_{nu}$).

wherein the system further comprises a preprocessing module, wherein the processing module eliminates the off instances using body impedance values prior to feature extraction and EE determination.

10. The system of claim 9, wherein the preprocessing module further comprises any of:

low-pass filtering the plurality of sensor streams; and normalize the plurality of sensor streams; and normalizing the plurality of sensor streams, wherein the normalized heart rate ($HR_{nu}$) is determined as any of a function of basal heart rate ($HR_b$), a function of maximal allowable heart rate ($HR_{max}$), and a fraction of heart rate reserve (HRR).

11. The system of claim 9, wherein the feature vector includes user/patient information related features that include any of height, weight, gender, age; heart rate related features that include any of heart rate (HR), normalized heart rate, and heart rate variability (HRV); and activity features that include signal magnitude area (SMA).

12. The system of claim 9, wherein the regression model is a piecewise linear regression model with a break point, wherein the break point is a function of a normalized heart rate ($HR_{nu}$) and is determined as a fraction of heart rate reserve (HRR), wherein the break point splits the determination of the EE into two separate linear regressions.

13. The system of claim 9, wherein the regression model is a piecewise linear regression model with two break points, wherein the two break points are a function of a normalized heart rate ($HR_{nu}$) and are each determined as a fraction of heart rate reserve (HRR), wherein the two break points split the determination of the EE into three separate linear regressions.

14. The system of claim 9, wherein the regression model is a nonlinear regression that does not include a break point.

* * * * *